United States Patent [19]

Rinehart

[11] 4,400,197

[45] Aug. 23, 1983

[54] N-(OPTIONALLY SUBSTITUTED 1,3-DIOXOLAN- OR DIOXAN-2-YLMETHYL)-N-ALKYL, ALKENYL, OR ALKYNYL-2,2-DICHLOROACETAMIDES

[75] Inventor: Jay K. Rinehart, Akron, Ohio

[73] Assignee: PPG Industries, Inc., Pittsburgh, Pa.

[21] Appl. No.: 276,309

[22] Filed: Jun. 22, 1981

Related U.S. Application Data

[62] Division of Ser. No. 106,434, Dec. 26, 1979, Pat. No. 4,294,764.

[51] Int. Cl.³ ............................................. A01N 25/32
[52] U.S. Cl. ............................................ 71/88; 71/100
[58] Field of Search ..................................... 71/88, 100

[56] References Cited

U.S. PATENT DOCUMENTS 2,913,327 11/1959 Tilles et al. ........................... 71/100
4,113,464 9/1978 Stach et al. ............................ 71/88
4,116,670 9/1978 Stach et al. ............................ 71/88
4,137,070 1/1979 Pallos ................................... 71/100

OTHER PUBLICATIONS

Pallos et al., J. Agr. and Food Chem. vol. 23 (1975) p. 821.
Hamm et al., Agr. and Food Chem. vol. 5 (1957) pp. 30-32.

Primary Examiner—Catherine L. Mills
Attorney, Agent, or Firm—Edward J. Whitfield; Robert J. Grassi

[57] ABSTRACT

Disclosed are antidotal compounds for use with active thiocarbamate and/or chloroacetanilide herbicides to control weeds without affecting crops such as corn and soybeans. Compositions of the antidote and the active thiocarbamates and/or chloroacetanilides are also disclosed.

10 Claims, No Drawings

N-(OPTIONALLY SUBSTITUTED 1,3-DIOXOLAN- OR DIOXAN-2-YLMETHYL)-N-ALKYL, ALKENYL, OR ALKYNYL-2,2-DICHLOROACETAMIDES

This is a division of application Ser. No. 106,434, filed Dec. 26, 1979 which issued on Oct. 13, 1981 as U.S. Pat. No. 4,294,764.

BACKGROUND OF THE INVENTION

1. Field of the Invention

The invention is to novel N-(optionally substituted 1,3-dioxolanor dioxan-2-ylmethyl-N-alkyl, alkenyl or alkynyl-2,2-dichloroacetamides described herein and their use as antidotes to protect crops from the phytotoxic effects of active thiocarbamate and/or chloroacetanilide herbicides.

2. Description of the Prior Art

Active thiocarbamate herbicides, such as EPTC, butylate, or vernolate, and/or chloroacetanilides are phytotoxic to certain crops, such as corn and soybeans. The compounds disclosed herein, when used in combination with the active thiocarbamates and/or chloroacetanilides, eliminate or prevent this phytotoxicity effect upon the crops so that the herbicides may be used to control weeds without affecting the crops, as described herein.

SUMMARY OF THE INVENTION

The invention concerns useful antidotes for active thiocarbamate and/or chloroacetanilide herbicides, graphically represented by Formula I:

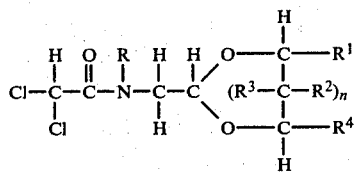

wherein R is ethyl, propyl, 1-methylethyl, 2-propenyl, 2-butenyl, 2-methyl-2-propenyl, 2-propynyl, or 1,1-dimethyl-2-propynyl; $R^1$, $R^2$, $R^3$, and $R^4$ are independently hydrogen or methyl; and n is zero (0) or one (1). For example, the compound N-(dioxolan-2-ylmethyl)-N-(2-propenyl)-2,2-dichloroacetamide is useful in compositions of an active thiocarbamate, such as EPTC, butylate, or vernolate, or a chloroacetanilide for controlling weeds in crops such as corn and/or soybeans.

DETAILED DESCRIPTION OF THE INVENTION

The novel agriculturally useful compounds which have antidotal properties when used to prevent phytotoxicity of active herbicidal thiocarbamates and/or chloroacetanilides on crops are graphically represented by Formula I:

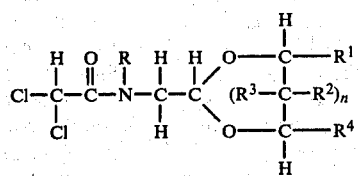

wherein:
R is ethyl, propyl, 1-methylethyl, 2-propenyl, 2-butenyl, 2-methyl-2-propenyl, 2-propynyl, or 1,1-dimethyl-2-propynyl; $R^1$, $R^2$, $R^3$, and $R^4$ are independently hydrogen or methyl; and
n is zero (0) or one (1).

Examples of compounds represented by Formula I are as follows:

a. n is one (1).
N-(1,3-dioxan-2-ylmethyl)-N-(1,1-dimethyl-2-propynyl)-2,2-dichloroacetamide
N-(1,3-dioxan-2-ylmethyl)-N-(2-propynyl)-2,2-dichloroacetamide
N-(1,3-dioxan-2-ylmethyl)-N-(2-methyl-2-propenyl)-2,2-dichloroacetamide
N-(1,3-dioxan-2-ylmethyl)-N-(2-butenyl)-2,2-dichloroacetamide
N-(1,3-dioxan-2-ylmethyl)-N-(2-propenyl)-2,2-dichloroacetamide
N-(1,3-dioxan-2-ylmethyl)-N-(1-methylethyl)-2,2-dichloroacetamide
N-(1,3-dioxan-2-ylmethyl)-N-propyl-2,2-dichloroacetamide
N-(1,3-dioxan-2-ylmethyl)-N-ethyl-2,2-dichloroacetamide
N-(4-methyl-1,3-dioxan-2-ylmethyl)-N-(1,1-dimethyl-2-propynyl)-2,2-dichloroacetamide
N-(4-methyl-1,3-dioxan-2-ylmethyl)-N-(2-propynyl)-2,2-dichloroacetamide
N-(4-methyl-1,3-dioxan-2-ylmethyl)-N-(2-methyl-2-propenyl)-2,2-dichloroacetamide
N-(4-methyl-1,3-dioxan-2-ylmethyl)-N-(2-butenyl)-2,2-dichloroacetamide
N-(4-methyl-1,3-dioxan-2-ylmethyl)-N-(2-propenyl)-2,2-dichloroacetamide
N-(4-methyl-1,3-dioxan-2-ylmethyl)-N-(1-methylethyl)-2,2-dichloroacetamide
N-(4-methyl-1,3-dioxan-2-ylmethyl)-N-propyl-2,2-dichloroacetatamide
N-(4-methyl-1,3-dioxan-2-ylmethyl)-N-ethyl-2,2-dichloroacetamide
N-(5-methyl-1,3-dioxan-2-ylmethyl)-N-(1,1-dimethyl-2-propynyl)-2,2-dichloroacetamide
N-(5-methyl-1,3-dioxan-2-ylmethyl)-N-(2-propynyl)-2,2-dichloroacetamide
N-(5-methyl-1,3-dioxan-2-ylmethyl)-N-(2-methyl-2-propenyl)-2,2-dichloroacetamide
N-(5-methyl-1,3-dioxan-2-ylmethyl)-N-(2-butenyl)-2,2-dichloroacetamide
N-(5-methyl-1,3-dioxan-2-ylmethyl)-N-(2-propenyl)-2,2-dichloroacetamide
N-(5-methyl-1,3-dioxan-2-ylmethyl)-N-(1-methylethyl)-2,2-dichloroacetamide
N-(5-methyl-1,3-dioxan-2-ylmethyl)-N-propyl-2,2-dichloroacetamide
N-(5-methyl-1,3-dioxan-2-ylmethyl)-N-ethyl-2,2-dichloroacetamide
N-(4,5-dimethyl-1,3-dioxan-2-ylmethyl)-N-(1,1-dimethyl-2-propynyl)-2,2-dichloroacetamide
N-(4,5-dimethyl-1,3-dioxan-2-ylmethyl)-N-(2-propynyl)-2,2-dichloroacetamide
N-(4,5-dimethyl-1,3-dioxan-2-ylmethyl)-N-(2-methyl-2-propenyl)-2,2-dichloroacetamide
N-(4,5-dimethyl-1,3-dioxan-2-ylmethyl)-N-(2-butenyl)-2,2-dichloroacetamide
N-(4,5-dimethyl-1,3-dioxan-2-ylmethyl)-N-(2-propenyl)-2,2-dichloroacetamide
N-(4,5-dimethyl-1,3-dioxan-2-ylmethyl)-N-(1-methylethyl)-2,2-dichloroacetamide N-(4,5-dimethyl-1,3-dioxan-2-ylmethyl)-N-propyl-2,2-dichloroacetamide
N-(4,5-dimethyl-1,3-dioxan-2-ylmethyl)-N-ethyl-2,2-dichloroacetamide
N-(4,6-dimethyl-1,3-dioxan-2-ylmethyl)-N-(1,1-dimethyl-2-propynyl)-2,2-dichloroacetamide
N-(4,6-dimethyl-1,3-dioxan-2-ylmethyl)-N-(2-propynyl)-2,2-dichloroacetamide
N-(4,6-dimethyl-1,3-dioxan-2-ylmethyl)-N-(2-methyl-2-propenyl)-2,2-dichloroacetamide
N-(4,6-dimethyl-1,3-dioxan-2-ylmethyl)-N-(2-butenyl)-2,2-dichloroacetamide
N-(4,6-dimethyl-1,3-dioxan-2-ylmethyl)-N-(2-propenyl)-2,2-dichloroacetamide
N-(4,6-dimethyl-1,3-dioxan-2-ylmethyl)-N-(1-methylethyl)-2,2-dichloroacetamide
N-(4,6-dimethyl-1,3-dioxan-2-ylmethyl)-N-propyl-2,2-dichloroacetamide
N-(4,6-dimethyl-1,3-dioxan-2-ylmethyl)-N-ethyl-2,2-dichloroacetamide
N-(5,5-dimethyl-1,3-dioxan-2-ylmethyl)-N-(1,1-dimethyl-2-propynyl)-2,2-dichloroacetamide
N-(5,5-dimethyl-1,3-dioxan-2-ylmethyl)-N-(2-propynyl)-2,2-dichloroacetamide
N-(5,5-dimethyl-1,3-dioxan-2-ylmethyl)-N-(2-methyl-2-propenyl)-2,2-dichloroacetamide
N-(5,5-dimethyl-1,3-dioxan-2-ylmethyl)-N-(2-butenyl)-2,2-dichloroacetamide
N-(5,5-dimethyl-1,3-dioxan-2-ylmethyl)-N-(2-propenyl)-2,2-dichloroacetamide
N-(5,5-dimethyl-1,3-dioxan-2-ylmethyl)-N-(1-methylethyl)-2,2-dichloroacetamide
N-(5,5-dimethyl-1,3-dioxan-2-ylmethyl)-N-propyl-2,2-dichloroacetamide
N-(5,5-dimethyl-1,3-dioxan-2-ylmethyl)-N-ethyl-2,2-dichloroacetamide
N-(4,5,6-trimethyl-1,3-dioxan-2-ylmethyl)-N-(1,1-dimethyl-2-propynyl)-2,2-dichloroacetamide
N-(4,5,6-trimethyl-1,3-dioxan-2-ylmethyl)-N-(2-propynyl)-2,2-dichloroacetamide
N-(4,5,6-trimethyl-1,3-dioxan-2-ylmethyl)-N-(2-methyl-2-propenyl)-2,2-dichloroacetamide
N-(4,5,6-trimethyl-1,3-dioxan-2-ylmethyl)-N-(2-butenyl)-2,2-dichloroacetamide
N-(4,5,6-trimethyl-1,3-dioxan-2-ylmethyl)-N-(2-propenyl)-2,2-dichloroacetamide
N-(4,5,6-trimethyl-1,3-dioxan-2-ylmethyl)-N-(1-methylethyl)-2,2-dichloroacetamide
N-(4,5,6-trimethyl-1,3-dioxan-2-ylmethyl)-N-propyl-2,2-dichloroacetamide
N-(4,5,6-trimethyl-1,3-dioxan-2-ylmethyl)-N-ethyl-2,2-dichloroacetamide
N-(4,5,5,6-tetramethyl-1,3-dioxan-2-ylmethyl)-N-(1,1-dimethyl-2-propynyl)-2,2-dichloroacetamide
N-(4,5,5,6-tetramethyl-1,3-dioxan-2-ylmethyl)-N-(2-propynyl)-2,2-dichloroacetamide
N-(4,5,5,6-tetramethyl-1,3-dioxan-2-ylmethyl)-N-(2-methyl-2-propenyl)-2,2-dichloroacetamide
N-(4,5,5,6-tetramethyl-1,3-dioxan-2-ylmethyl)-N-(2-butenyl)-2,2-dichloroacetamide
N-(4,5,5,6-tetramethyl-1,3-dioxan-2-ylmethyl)-N-(2-propenyl)-2,2-dichloroacetamide
N-(4,5,5,6-tetramethyl-1,3-dioxan-2-ylmethyl)-N-(1-methylethyl)-2,2-dichloroacetamide
N-(4,5,5,6-tetramethyl-1,3-dioxan-2-ylmethyl)-N-propyl-2,2-dichloroacetamide
N-(4,5,5,6-tetramethyl-1,3-dioxan-2-ylmethyl)-N-ethyl-2,2-dichloroacetamide b. n is zero (0).
N-(1,3-dioxolan-2-ylmethyl)-N-(1,1-dimethyl-2-propynyl)-2,2-dichloroacetamide
N-(1,3-dioxolan-2-ylmethyl)-N-(2-propynyl)-2,2-dichloroacetamide
N-(1,3-dioxolan-2-ylmethyl)-N-(2-methyl-2-propenyl)-2,2-dichloroacetamide
N-(1,3-dioxolan-2-ylmethyl)-N-(2-butenyl)-2,2-dichloroacetamide
N-(1,3-dioxolan-2-ylmethyl)-N-(2-propenyl)-2,2-dichloroacetamide
N-(1,3 dioxolan-2-ylmethyl)-N-(1-methylethyl)-2,2-dichloroacetamide
N-(1,3-dioxolan-2-ylmethyl)-N-propyl-2,2-dichloroacetamide
N-(1,3-dioxolan-2-ylmethyl)-N-ethyl-2,2-dichloroacetamide
N-(4-methyl-1,3-dioxolan-2-ylmethyl)-N-(1,1-dimethyl-2-propynyl)-2,2-dichloroacetamide
N-(4-methyl-1,3-dioxolan-2-ylmethyl)-N-(2-propynyl)-2,2-dichloroacetamide
N-(4-methyl-1,3-dioxolan-2-ylmethyl)-N-(2-methyl-2-propenyl)-2,2-dichloroacetamide
N-(4-methyl-1,3-dioxolan-2-ylmethyl)-N-(2-butenyl)-2,2-dichloroacetamide
N-(4-methyl-1,3-dioxolan-2-ylmethyl)-N-(2-propenyl)-2,2-dichloroacetamide
N-(4-methyl-1,3-dioxolan-2-ylmethyl)-N-(1-methylethyl)-2,2-dichloroacetamide
N-(4-methyl-1,3-dioxolan-2-ylmethyl)-N-propyl-2,2-dichloroacetamide
N-(4-methyl-1,3-dioxolan-2-ylmethyl)-N-ethyl-2,2-dichloroacetamide
N-(4,5-dimethyl-1,3-dioxolan-2-ylmethyl)-N-(1,1-dimethyl-2-propynyl)-2,2-dichloroacetamide
N-(4,5-dimethyl-1,3-dioxolan-2-ylmethyl)-N-(2-propynyl)-2,2-dichloroacetamide
N-(4,5-dimethyl-1,3-dioxolan-2-ylmethyl)-N-(2-methyl-2-propenyl)-2,2-dichloroacetamide
N-(4,5-dimethyl-1,3-dioxolan-2-ylmethyl)-N-(2-butenyl)-2,2-dichloroacetamide
N-(4,5-dimethyl-1,3-dioxolan-2-ylmethyl)-N-(2-propenyl)-2,2-dichloroacetamide
N-(4,5-dimethyl-1,3-dioxolan-2-ylmethyl)-N-(1-methylethyl)-2,2-dichloroacetamide
N-(4,5-dimethyl-1,3-dioxolan-2-ylmethyl)-N-propyl-2,2-dichloroacetamide
N-(4,5-dimethyl-1,3-dioxolan-2-ylmethyl)-N-ethyl-2,2-dichloroacetamide Although all of the compounds defined herein are useful for the purposes disclosed herein, some are better than others. In general, the compounds in which n is one (1) are useful, and it is generally preferred that $R^1$, $R^2$, $R^3$, and $R^4$ be the same. The compounds in which $R^1$ and $R^4$ are hydrogen and $R^2$ and $R^3$ are methyl are very useful, but it is preferred that $R^1$, $R^2$, $R^3$, and $R^4$ be hydrogen. The more preferred compounds are those in which n is zero (0). It is highly preferred that $R^1$ and $R^4$ be the same, and it is especially preferred that $R^1$ and $R^4$ be hydrogen. The order of preference for R is as follows: 2-propenyl is most preferred, followed by 1-methylethyl, propyl, ethyl, 2-butenyl, 2-methyl-2-propenyl, 2-propynyl, and 1,1-dimethyl-2-propynyl. The most preferred compound described herein is N-(1,3-dioxolan-2-ylmethyl)-N-(2-propenyl)-2,2-dichloroacetamide.

A. General Synthesis of the Compounds

The compounds described herein are generally prepared by any of the general synthesis methods described herein. Formula I can be prepared by reacting an amine of Formula II:

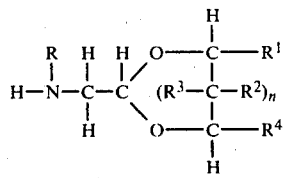 (II)

wherein R, n, R¹, R², R³, and R⁴ are as heretofore described, with dichloroacetylchloride in an inert, organic reaction medium such as benzene or dichloromethane, in the presence of an acid acceptor such as a tertiary amine or an alkaline metal carbonate or hydroxide at a temperature of about −10° Centigrade to about 25° Centigrade and stirring the resulting mixture for a period of about 15 to 120 minutes. After this time the reaction mixture can be washed with water to remove inorganic salts and stripped of solvent to yield the desired product. This product can then be used as such or can be further purified by conventional means.

The compounds of Formula II can be prepared by reacting an excess molar amount of a substituted amine of Formula III:

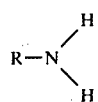 (III)

wherein R is an heretofore described, with a compound of Formula IV:

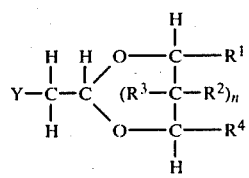 (IV)

wherein Y is chlorine or bromine; and n, R¹, R², R³, and R⁴ are as described herein. The mixture of the reactants is heated with agitation for a period of about one-half to 120 hours. Whenever a low-boiling amine is used, preferably a pressurized vessel is used. After this time, a strong inorganic base, as an aqueous base (such as sodium hydroxide), is added to the reaction mixture to liberate the free amine from its hydrochloride. The organic phase is then separated from the aqueous phase, dried over a suitable drying agent and distilled to yield the desired product.

When the compounds of Formula IV are not available, they can be prepared by reacting an acetal of Formula V:

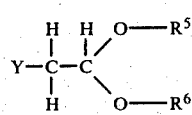 (V)

wherein Y is as described herein, and R⁵ and R⁶ are methyl or ethyl, with a diol of Formula VI:

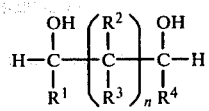 (VI)

wherein R¹, R², R³, R⁴, and n are as described herein. The reaction is effected by combining the compound of Formula V with a compound of Formula VI in about equimolar amounts and in the presence of an acid catalyst such as sulfuric acid or p-toluenesulfonic acid under anhydrous conditions. The mixture can be heated at reflux for a period of about one (1) to about four (4) hours. After this time the reaction mixture can be distilled under reduced pressure to yield the desired product.

Another method of forming the compounds of Formula I is by reacting an acetal of Formula VII:

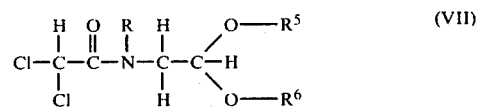 (VII)

wherein R⁵ and R⁶ are as defined herein with about an equimolar amount of a diol of Formula VI. This reaction can be effected by combining the reactants in the presence of a catalytic amount of p-toluenesulfonic acid under anhydrous conditions. The reaction mixture can be heated and the alcohol removed by distillation as it is formed. After no more alcohol is given off, sodium carbonate can be added to neutralize the acid catalyst and the reaction mixture distilled to yield the desired product.

The compounds of Formula VII can be prepared by reacting a compound of Formula VIII:

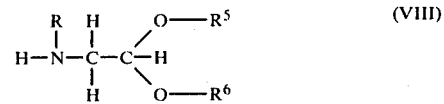 (VIII)

wherein R, R⁵ and R⁶ are as described herein, with dichloroacetylchloride. This reaction can be carried out in the same manner as the reaction between the compound of Formula II with the dichloroacetylchloride.

The compounds of Formula VIII can be prepared by reacting the amine of Formula III with about an equimolar amount of the acetal of Formula V. This reaction can be effected by combining the reactants in an inert organic reaction medium as defined herein and in the presence of an acid acceptor as defined herein. The reaction mixture can be heated at reflux for a period of from 2 to 120 hours. After this time, the mixture is filtered and stripped of solvent to yield the desired product.

Examples of suitable diols of Formula VI for preparing the compounds of the present invention are: 1,2-ethanediol; 1,2-propanediol; 2,3-butanediol; 1,3-propanediol; 1,3-butanediol; 2-methyl-1,3-propanediol; 2-methyl-1,3-butanediol; 2,4-pentanediol; 2,2-dimethyl-1,3-propanediol; 3-methyl-2,4-pentanediol; 3,3-dimethyl-2,4-pentanediol; and the like. Examples of suitable amines of Formula IV are: methylamine, ethylamine, propylamine, isopropylamine, 2-propenylamine, 2-butenylamine, 2-methyl-2-propenylamine, 2-propynylamine (also called propargylamine), and 1,1-dimethyl-2-propynylamine (also called 1,1-dimethylpropargylamine).

The following examples illustrate the synthesis of the compounds described herein.

EXAMPLE I

N-(1,3-dioxolan-2-ylmethyl)-N-(2-propenyl)-2,2-dichloroacetamide

N-(2,2-dimethoxyethyl)-N-(2-propenyl)-2,2-dichloroacetamide (15.00 grams, 0.059 mole), ethylene glycol (6.2 grams, 0.1 mole), and p-toluenesulfonic acid catalyst (2 crystals) were heated in a round-bottomed flask for four hours at approximately 110° Centigrade. The methanol generated was distilled off, the reaction mixture cooled and poured into dichloromethane (100 milliliters). The solution was washed with 10 percent aqueous sodium hydroxide (50 milliliters), water (two separate, 100-milliliter portions), and dried over sodium sulfate. The solvent was removed under vacuum on a rotary evaporator to give 13.18 grams (88.6 percent yield) of a dark liquid of N-(1,3-dioxlan-2-ylmethyl)-N-(2-propenyl)-2,2-dichloroacetamide. The infrared (IR) spectrum (NEAT) showed the characteristic amide carbonyl absorption at 1675 cm$^{-1}$. Nuclear magnetic resonance (NMR) in CDCl$_3$ showed $\delta$3.40–3.68, m, —CH$_2$CH=CH$_2$; $\delta$3.93, s, —CH$_2$CH$_2$; $\delta$3.93–4.33, m, —CH$_2$CH; $\delta$4.95–6.10, m, —CH=CH$_2$; $\delta$4.95–5.20, m, CH; $\delta$6.73, CHCl$_2$.

B. Herbicidal Compositions

The compounds disclosed herein are useful, when combined with active thiocarbamate herbicide compounds like those described herein, such as ethiolate (S-ethyl diethylthiocarbamate) but preferably with the active herbicidal thiocarbamates of butylate (S-ethyl diisobutylthiocarbamate), EPTC (S-ethyl dipropylthiocarbamate), and/or vernolate (S-propyl dipropylthiocarbamate). In general, the antidotal compounds are present in an amount of one part by weight of the antidote to from 6 to 18 parts by weight of the active thiocarbamate herbicidal compound. One or more of the antidotal compounds described herein may be used and these may be in a mixture varying from 0.01 to 1 part by weight to each other. The most preferred herbicidal compositions are those in which the active thiocarbamate is one of the preferred thiocarbamates described herein in combination with the most preferred antidotal compound of N-(1,3-dioxolan-2-ylmethyl)-N-(2-propenyl)-2,2-dichloroacetamide.

The antidotal compounds of the Formula I described herein are useful when combined with an active chloroacetanilide herbicidal compound like those described herein, to prevent injury to crops which are sensitive to the active chloroacetanilide herbicidal compound. The compositions are comprised of an active chloroacetanilide and one or more antidotal compounds which are effective with the chloroacetanilide. The preferred chloroacetanilide herbicidal compounds are those of 2-chloro-2',6'-diethyl-N-(methoxymethyl)acetanilide (alachlor), 2-chloro-N-isopropylacetanilide (propachlor), 2-chloro-N,N-diallylacetamide (CDAA), N-chloroacetyl-N-(2,6-diethylphenyl)-glycine ethyl ester (Hercules 22234), 2-chloro-N-(2-ethyl-6-methylphenyl)-N-(2-methoxy-1-methylethyl)acetamide (metolachlor), and 2-chloro-2',3'-dimethyl-N-(methoxymethyl)acetanilide. In general, the antidotal compounds are present in an amount of one part by weight of the antidote to from 6 to 18 parts by weight of the active chloroacetanilide herbicidal compound. One or more of the antidotal compounds described herein may be used, and these may be in a mixture varying from 0.01 to 1 part by weight of the antidote to each other. The most preferred herbicidal compositions are those in which the active chloroacetanilide is one of the preferred chloroacetanilides described herein in combination with the most preferred antidotal compound.

C. Method of Controlling the Weeds

The antidotal compounds of the present invention can be used in any convenient form. Thus, the antidote compounds can be made into emulsifiable liquids, emulsifiable concentrates, liquid, wettable powder, or adsorbed on powders or granules, or any other convenient form. In its preferred form, the antidotal compounds are admixed with the active thiocarbamates or chloroacetanilides and incorporated into the soil prior to planting the seed. It is to be understood, however, that the thiocarbamate herbicide or chloroacetanilide herbicide can be incorporated into the soil, and then the antidotal compound can be incorporated into the soil, the depth of incorporation being from one to four inches prior to planting. Moreover, the seed can be treated with the antidotal compound and planted into the soil which has been treated with herbicides or untreated with a herbicide and subsequently treated with a herbicide. The method of addition of the antidotal compound does not affect the herbicidal activity of the thiocarbamate or the chloroacetanilide compounds against weeds.

The exact amount of antidotal compound will usually be determined on economic ratios for the most effective amount usable.

When used in the claims of this application, the phrase "active thiocarbamate herbicidal compounds" or "active chloroacetanilide herbicidal compounds" is meant to include the active thiocarbamates or chloroacetanilide alon or admixed with other active compounds such as the S-triazines, and 2,4-D, or the active acetanilides and the like. Also, the active thiocarbamate or chloroacetanilide compound is different from the antidotal compound. Note the phrase "contacting the weeds" with a herbicidally effective amount of an active thiocarbamate or chloroacetanilide herbicidal compound described herein means any method whereby the weeds are contacted as stated herein, and the phrase "contacting the crop with an antidotally effective amount of the antidotal compound of the formula described herein" means any method of contacting the crop with an effective antidotal compound as mentioned herein. The phrase "an antidotally effective amount of an antidotal compound of the formula" refers to that amount which will protect the crop from substantial injury, that is, the injury to the crop will be less than 20 percent. The most important crops for protection defined herein are those of corn and soybeans, which are sensitive to the active herbicide, as well as other crops which are sensitive. A herbicidally effective amount of an active thiocarbamate herbicidal compound or an active chloroacetanilide herbicidal compound means that amount of the herbicide whereby the weeds, that is, the undesirable plants, are either killed or so severely injured that they do not recover and do not complete with the crop for growth, space, and nutrients.

The preferred method is by incorporating into the soil prior to planting one of the herbicidal compositions described herein.

The effectiveness and use of the antidotal compounds described herein and compositions described herein are shown by the following examples, which were conducted in the following manner.

Soil Incorporation

Pulverized, sandy loam topsoil and coarse, washed cement and screened to pass a 3/16-inch mesh screen were mixed in a ratio of three parts of soil to one part of sand, and the mix was Pasteurized with live steam to kill plants, pathogenic organisms, and natural weed seed populations.

Small flats were filled within ⅜ inch of the top with the Pasteurized soil mixture, leveled but not firmed, and were passed under a herbicide sprayer equipped with a fixed nozzle suspended over a movable belt with speed adjustment. An 800IE fan nozzle operated at 40 PSI air pressure, delivering 25 milliliters of distilled water in 4.6 seconds. At 10 inches above the soil surface, an 18-inch wide spray pattern was applied. The belt travelled 30 inches per revolution in 8.3 seconds, which is equivalent to 0.616 miles per hour. The soil test containers passed under the nozzle within 4.6 seconds. The area covered in this time is 6.75 square feet. The volume of liquid delivered is equivalent to 42.6 gallons per acre. A 0.7029 gram of a 100 percent active material per 6.75 square feet is equivalent to ten pounds of active ingredient per acre. Formulations of commercial thiocarbamates and antidotes used water as the solvent system. Other formulations used a standard solvent mixture of acetone: methanol:dimethylformamide, 90:8:2 (V/V), to formulate all of the tank mixtures of two or more compounds, which were thoroughly mixed in the common carrier before dilution as required to the appropriate amount for spraying. The mixture was prepared 15 minutes prior to application. After the test container was sprayed, it was immediately emptied into a clean plastic bag, the top secured, and the contents thoroughly mixed by hand agitation of the plastic bag. The contents were then emptied back into the test container and set aside until all treatments had been applied. The soil was then leveled, firmed, and seeded with Funk's G 4288 Hybrid Field Corn and the soil mixture covered with a 1-inch layer of Pasteurized screened sand. The treated flats were then moved into the plant growth room, where they were lightly watered overhead as required to insure growth. The plant growth room was illuminated with a light intensity that averaged 2,500 candles at the growth level. The room operated at 84 to 86 degrees Fahrenheit during the 16-hour photo period, and 70 to 74 degrees Fahrenheit at night. The relative humidity of the room when less than 33 percent full was at 50 to 55 percent.

The treated flats were allowed to grow and the injury to the corn was rated after specific periods of time. The injury was noted as reduction in growth, and/or as hormonal distortion. This hormone injury is manifested as a distortion of the growing apex of the stem due to the failure of the developing leaves to unfurl from the growing shoot. Continued apical growth results in a compaction and distortion of the subapical tissues until a break is caused in the surrounding leaf tissue. Injury may occur in the initial seedling stages of growth when high concentrations of thiocarbamates have been applied, or at later growth stages with lower concentration of the herbicide. The distortion may not appear until the growing apex of the stem is above the soil line or may not appear until the apex divides and begins formation of the pistillate inflorescens. Injury may also cause weakening of the prop root system causing the whole plant to fall over with its own weight.

EXAMPLE II

When EPTC (S-ethyl dipropylthiocarbamate) was applied by preplant incorporation at 6 pounds per acre, with no antidotal compound added, as described above, the corn showed a 90 percent injury as reduction in growth and hormonal distortion after 17 days, 24 days, and 51 days. In addition, after 51 days, necrosis also developed to contribute to the injury of the corn crop.

EXAMPLE III

When EPTC at 6 pounds per acre and N-(1,3-dioxolan-2-ylmethyl)-N-(2-propenyl)-2,2-dichloroacetamide (from Example I) at 1.0 pounds per acre, that is, a ratio of 6 parts by weight of EPTC to one part by weight of the antidote, were applied as described above, the corn crop, after 17, 24, and 51 days was completely healthy and normal.

EXAMPLE IV

When EPTC at 6 pounds per acre and N-(1,3-dioxolan-2-ylmethyl)-N-methyl-2,2-dichloroacetamide at 1.0 pounds per acre corresponding to a weight ratio of 6 parts of EPTC to 1 part of weight of antidote was applied as described above, after 36 days the corn was 50 percent injured by reduction in growth and hormonal distortion. After 48 days, there was no evidence of recovery of the corn, and the percent of injury had risen to 60 percent.

While the invention has been described by reference through the specific details of certain illustrative embodiments, it is not intended that it shall be limited thereby, except insofar as such appear in the accompanying claims.

I claim:

1. A composition containing:
   (a) a herbicidally effective amount of N-dialkyl thiocarbamate; and
   (b) an antidotally effective amount of a compound represented by the formula:

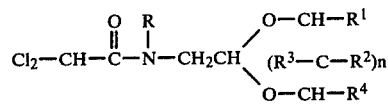

wherein:
R is ethyl, propyl, 1-methylethyl, 2-propenyl, butenyl, 2-methyl-2-propenyl, 2-propynyl or 1,1-dimethyl-2-propynyl;
$R^1$, $R^2$, $R^3$ and $R^4$ are independently hydrogen or methyl; and
n is 0 or 1.

2. The composition of claim 1 wherein N-dialkyl thiocarbamate herbicide is selected from S-ethyl dipropylthiocarbamate, S-ethyl diisobutylthiocarbamate, S-propyl dipropylthiocarbamate or S-ethyl diethylthiocarbamate.

3. The composition of claim 1 wherein the weight ratio of N-dialkyl thiocarbamate herbicide to antidotal compound ranges from 18:1 to 6:1.

4. The composition of claim 1 wherein the antidotal compound is N-(1,3-dioxolan-2-ylmethyl)-N-(2-propenyl)-2,2-dichloroacetamide.

5. In a method of controlling weed growth among crops wherein a herbicidally effective amount of N-dialkyl thiocarbamate herbicide is used to control said weeds, the improvement residing in controlling said weeds with said S-alkyl thiocarbamate herbicide in the presence of an antidotally effective amount of an antidotal compound represented by the formula:

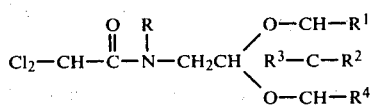

wherein:

R is ethyl, propyl, 1-methylethyl, 2-propenyl, 2-butenyl, 2-methyl-2-propenyl, 2-propynyl or 1,1-dimethyl-2-propynyl;

$R^1$, $R^2$, $R^3$ and $R^4$ are independently hydrogen or methyl; and n is 0 or 1 to reduce the phytotoxic effect of the S-alkyl thiocarbamate on said crops.

6. The improvement of claim 5 wherein the weight ratio of N-dialkyl thiocarbamate herbicide to antidotal compound ranges from 18:1 to 6:1.

7. The improvement of claim 5 wherein the N-dialkyl thiocarbamate herbicide is selected from S-ethyl dipropylthiocarbamate, S-ethyl diisobutylthiocarbamate, S-propyl dipropylthiocarbamate or S-ethyl diethylthiocarbamate.

8. The improvement of claim 5 wherein the antidotal compound is N-(1,3-dioxolan-2-ylmethyl)-N-(2-propenyl)-2,2-dichloroacetamide.

9. A composition containing a herbicidally effective amount of S-ethyl diisopropyl thiocarbamate herbicide and an antidotally effective amount of N-(1,3-dioxolan-2-ylmethyl)-N-(2-propenyl)-2,2-dichloroacetamide.

10. In a method of controlling weed growth in a corn crop wherein a herbicidally effective amount of S-ethyl diisopropyl thiocarbamate herbicide is used to control the weed growth, the improvement residing in controlling said weed growth with said S-ethyl diisopropyl thiocarbamate in the presence of an antidotally effective amount of N-(1,3-dioxolan-2-ylmethyl)-N-(2-propenyl)-2,2-dichloroacetamide to reduce the phytotoxic effect of the S-ethyl diisopropyl thiocarbamate on the corn.

* * * * *

UNITED STATES PATENT AND TRADEMARK OFFICE
CERTIFICATE OF CORRECTION

PATENT NO. : 4,400,197

DATED : August 23, 1983

INVENTOR(S) : Jay K. Rinehart

It is certified that error appears in the above-identified patent and that said Letters Patent is hereby corrected as shown below:

The formula at column 10, line 50 and at column 11, line 15 should read as follows:

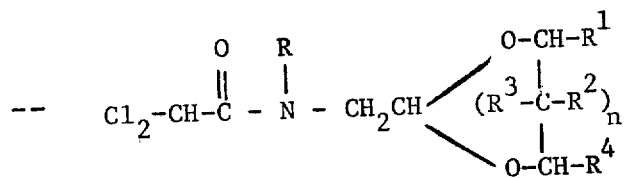

Signed and Sealed this

Thirteenth Day of December 1983

[SEAL]

Attest:

GERALD J. MOSSINGHOFF

Attesting Officer     Commissioner of Patents and Trademarks